(12) United States Patent
Takahashi et al.

(10) Patent No.: US 11,034,634 B2
(45) Date of Patent: Jun. 15, 2021

(54) METHOD FOR PRODUCING FLUOROHALOGENATED HYDROCARBON

(71) Applicant: DAIKIN INDUSTRIES, LTD., Osaka (JP)

(72) Inventors: Kazuhiro Takahashi, Osaka (JP); Tatsuya Takakuwa, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 128 days.

(21) Appl. No.: 16/481,300

(22) PCT Filed: Jan. 31, 2018

(86) PCT No.: PCT/JP2018/003213
§ 371 (c)(1),
(2) Date: Jul. 26, 2019

(87) PCT Pub. No.: WO2018/143271
PCT Pub. Date: Aug. 9, 2018

(65) Prior Publication Data
US 2021/0130267 A1    May 6, 2021

(30) Foreign Application Priority Data
Jan. 31, 2017  (JP) .............. JP2017-015587

(51) Int. Cl.
*C07C 17/20* (2006.01)
*C07C 17/383* (2006.01)
(Continued)

(52) U.S. Cl.
CPC ............ *C07C 17/206* (2013.01); *C07C 17/25* (2013.01); *C07C 17/263* (2013.01); *C07C 17/38* (2013.01); *C07C 17/383* (2013.01); *C07C 21/18* (2013.01)

(58) Field of Classification Search
CPC ..... C07C 17/206; C07C 17/383; C07C 17/38; C07C 21/18; C07C 17/25; C07C 17/263
See application file for complete search history.

(56) References Cited

U.S. PATENT DOCUMENTS

2015/0080619 A1    3/2015  Deur-Bert et al.

FOREIGN PATENT DOCUMENTS

WO    2007/079431    7/2007
WO    2013/111911    8/2013
(Continued)

OTHER PUBLICATIONS

International Search Report dated Mar. 13, 2018 in International (PCT) Application No. PCT/JP2018/003213.
(Continued)

*Primary Examiner* — Jafar F Parsa
(74) *Attorney, Agent, or Firm* — Wenderoth, Lind & Ponack, L.L.P.

(57) ABSTRACT

A method for producing a fluorine-containing halogenated hydrocarbon comprising reacting a chlorine-containing compound and hydrogen fluoride in a vapor phase, and a separation step of separating a reaction product containing hydrogen fluoride, hydrogen chloride, and organic matter containing the fluorine-containing halogenated hydrocarbon into multiple components, the separation step comprising: separating the reaction product into a gas phase and a liquid phase, increasing the pressure of the liquid phase and supplying the liquid phase into a distillation column, compressing the gas phase and supplying the gas phase into the distillation column, separating a first stream containing the hydrogen chloride from the top of the distillation column, and separating a second stream containing the organic matter and the hydrogen fluoride from the bottom of the distillation column. The method is for stably obtaining a (Continued)

target compound by preventing hydrogen fluoride contained in the outlet gas from condensing during compression.

8 Claims, 1 Drawing Sheet

(51) Int. Cl.
    *C07C 17/25*     (2006.01)
    *C07C 17/38*     (2006.01)
    *C07C 17/263*    (2006.01)
    *C07C 21/18*     (2006.01)

(56) References Cited

FOREIGN PATENT DOCUMENTS

| | | |
|---|---|---|
| WO | 2013/114015 | 8/2013 |
| WO | 2013/141409 | 9/2013 |

OTHER PUBLICATIONS

Extended European Search Report dated Apr. 26, 2021 in corresponding European Application No. 18748736.8.

METHOD FOR PRODUCING FLUOROHALOGENATED HYDROCARBON

TECHNICAL FIELD

The present invention provides a method for producing at least one fluorine-containing halogenated hydrocarbon selected from the group consisting of 1,1,1,2,2-pentafluoropropane (HFC-245cb), 1,1,1,3,3-pentafluoropropane (HFC-245fa), E,Z-1,3,3,3-tetrafluoropropene (E,Z-HFO-1234ze), 2,3,3,3-tetrafluoropropene (HFO-1234yf), 2-chloro-3,3,3-trifluoropropene (HCFO-1233xf), and 1-chloro-3,3,3-trifluoropropene (HCFO-1233zd), the method being a production method for stably obtaining a target compound, Fluorine-containing halogenated hydrocarbons obtained in the present invention include fluorinated hydrocarbons that contain fluorine as a halogen as well as fluorine-containing halogenated hydrocarbons that contain other halogens in addition to fluorine.

BACKGROUND ART

Fluorine-containing halogenated hydrocarbons, such as HFC-245cb, HFC-245fa, E,Z-HFO-1234ze, HFO-1234yf, HCFO-1233xf, and HCFO-1233zd have been conventionally used in various applications, such as a heat medium (refrigerant), foaming agent, solvent, detergent, propellant, and fire extinguisher. It is known that such fluorine-containing halogenated hydrocarbons are produced by reacting a chlorine-containing compound and hydrogen fluoride in the presence of a catalyst in a vapor phase. Specifically, as a method for producing HFO-1234yf, which is considered to be promising as a refrigerant for car air conditioners because of its low global warming potential (GWP), the following various methods are disclosed.

For example, Patent Literature 1 and 2 disclose a method for producing 2-chloro-3,3,3-trifluoropropene (HCFO-1233xf) and HFO-1234yf by vapor-phase fluorination reaction using 1,1,1,2,3-pentachloropropane (HCC-240db) as a starting material, and anhydrous hydrogen fluoride and a catalyst. Patent Literature 3 discloses a method for producing HFO-1234yf by vapor-phase fluorination reaction using 1,1,2,3-tetrachloropropene (HCO-1230xa) as a starting material, and anhydrous hydrogen fluoride and a catalyst.

Vapor-phase fluorination reaction using a catalyst has a problem of catalyst deactivation caused by repeated reaction. Such a catalyst deactivation problem is significant when a starting material having a double bond, such as HCFO-1233xf, is used because it is likely to become a catalyst poison. Accordingly, Patent Literature 4, for example, discloses adding oxygen or chlorine to a fluorination reactor to inhibit catalyst deactivation.

Catalyst deactivation is apparently affected by the concentration of a starting material (starting material organic matter). In order to reduce the concentration of the starting material to inhibit catalyst deactivation, a method for increasing the excess percentage of hydrogen fluoride or a method for reducing the reaction pressure in fluorination reaction is known. Reduction in reaction pressure reduces the condensation temperature in the condenser of a distillation column used for removing a side product such as hydrogen chloride, which increases equipment cost and other costs.

CITATION LIST

Patent Literature

PTL 1: Pamphlet of WO2013/141409
PTL 2: Pamphlet of WO2013/111911
PTL 3: Pamphlet of WO2007/079431
PTL 4: Pamphlet of WO2013/114015

SUMMARY OF INVENTION

Technical Problem

To solve the above problem, one option is a method for compressing gas at the outlet of a fluorination reactor using a compressor to increase the condensation temperature in a condenser. However, a hydrogen fluoride-containing gas may reduce its temperature and condense by compression. This is because when hydrogen fluoride is in a stable state, 6 molecules are associated, and hydrogen fluoride is likely to condense by heat absorbed during compression. Condensation not only makes compression difficult but also may break the compressor in the worst case.

The present invention solves these problems, and aims to provide a method for producing a fluorine-containing halogenated hydrocarbon, comprising the step of compressing gas at the outlet of a fluorination reactor using a compressor, wherein the method is for stably obtaining a target compound by preventing hydrogen fluoride contained in the outlet gas from condensing during compression.

Solution to Problem

As a result of extensive research to achieve the above object, the present inventors found that the object can be attained by a method for producing a fluorine-containing halogenated hydrocarbon comprising a specific separation step of separating a reaction product (gas at the outlet of a fluorination reactor) containing hydrogen fluoride, hydrogen chloride, and organic matter containing a fluorine-containing halogenated hydrocarbon into multiple components. The present invention was thus accomplished.

Specifically, the present invention relates to the following method for producing a fluorine-containing halogenated hydrocarbon.

1. A method for producing a fluorine-containing halogenated hydrocarbon comprising the step of reacting a chlorine-containing compound and hydrogen fluoride in a vapor phase,
the method comprising a separation step of separating a reaction product containing hydrogen fluoride, hydrogen chloride, and organic matter containing the fluorine-containing halogenated hydrocarbon into multiple components,
the fluorine-containing halogenated hydrocarbon being at least one member selected from the group consisting of 1,1,1,2,2-pentafluoropropane (HFC-245cb), 1,1,1,3,3-pentafluoropropane (HFC-245fa), E,Z-1,3,3,3-tetrafluoropropene (E,Z-HFO-1234ze), 2,3,3,3-tetrafluoropropene (HFO-1234yf), 2-chloro-3,3,3-trifluoropropene (HCFO-1233xf), and 1-chloro-3,3,3-trifluoropropene (HCFO-1233zd),
the separation step comprising:
(1) step 1 of separating the reaction product into a gas phase and a liquid phase,
(2) step 2 of increasing the pressure of the liquid phase and supplying the liquid phase into a distillation column A,
(3) step 3 of compressing the gas phase and supplying the gas phase into the distillation column A, and
(4) step 4 of separating a first stream containing the hydrogen chloride from the top of the distillation column A, and separating a second stream containing the organic matter and the hydrogen fluoride from the bottom of the distillation column A, (5) in step 3, the gas phase being compressed in series in two or more stages using a compressor, and heated by a heater to maintain a fraction of compressed gas at each stage of 1.

2. The method according to Item 1, wherein the chlorine-containing compound is at least one member of chlorine-containing alkanes or chlorine-containing alkenes.

3. The method according to claim 1, wherein the chlorine-containing compound is at least one member selected from the group consisting of 1,1,1,2,3-pentachloropropane (HCC-240db), 1,1,2,2,3-pentachloropropane (HCC-240aa), 1,1,2,3-tetrachloropropene (HCO-1230xa), 2,3,3,3-tetrachloropropene (HCO-1230xf), 2-chloro-3,3,3-trifluoropropene (HCFO-1233xf), 2,3-dichloro-3,3-difluoropropene (HCFO-1232xf), 1,2,3-trichloro-1,1-difluoropropane (HCFC-242dc), 1-chloro-3,3,3-trifluoropropene (HCFO-1233zd), 2,3-dichloro-1,1,1-trifluoropropane (HCFC-243db), 3,3-dichloro-1,1,1-trifluoropropane (HCFC-243fa), 2-chloro-1,1,1,2-tetrafluoropropane (HCFC-244bb), and 3-chloro-1,1,1,3-tetrafluoropropane (HCFC-244fa).

4. The method according to Item 1, wherein the fluorine-containing halogenated hydrocarbon comprises HFO-1234yf, and the chlorine-containing compound is at least one member selected from the group consisting of 1,1,1,2,3-pentachloropropane (HCC-240db), 1,1,2,2,3-pentachloropropane (HCC-240aa), 1,1,2,3-tetrachloropropene (HCO-1230xa), 2,3,3,3-tetrachloropropene (HCO-1230xf), 2-chloro-3,3,3-trifluoropropene (HCFO-1233xf), 2,3-dichloro-3,3-difluoropropene (HCFO-1232xf), 1,2,3-trichloro-1,1-difluoropropane (HCFC-242dc), 1-chloro-3,3,3-trifluoropropene (HCFO-1233zd), and 2,3-dichloro-1,1,1-trifluoropropane (HCFC-243db).

5. The method according to Item 1, wherein the fluorine-containing halogenated hydrocarbon comprises HFO-1234yf, and the chlorine-containing compound comprises HCFO-1233xf.

6. The method according to any one of Items 1 to 5, wherein the molar ratio of the hydrogen fluoride to the chlorine-containing compound at the beginning of the reaction of the chlorine-containing compound and the hydrogen fluoride in a vapor phase is 10 or more.

7. The method according to any one of Items 1 to 6, wherein when the gas phase is compressed in series in two or more stages in step 3, the compression rate at each stage is 2 times or more.

8, The method according to any one of Items 1 to 7, further comprising the step of supplying the second stream into a distillation column B, and separating the second stream into a third stream containing the fluorine-containing halogenated hydrocarbon and a fourth stream containing the hydrogen fluoride and organic matter other than the fluorine-containing halogenated hydrocarbon by distillation.

Advantageous Effects of Invention

According to the production method of the present invention, in an embodiment in which reaction pressure in a fluorination reaction is reduced to inhibit catalyst deactivation, and gas at the outlet of a fluorination reactor is compressed using a compressor, condensation of hydrogen fluoride contained in the gas at the reactor outlet can be prevented, thus leading to the subsequent distillation step. Accordingly, a fluorine-containing halogenated hydrocarbon, which is a target compound, can be stably obtained without breaking the compressor.

DESCRIPTION OF EMBODIMENTS

Figure 1:
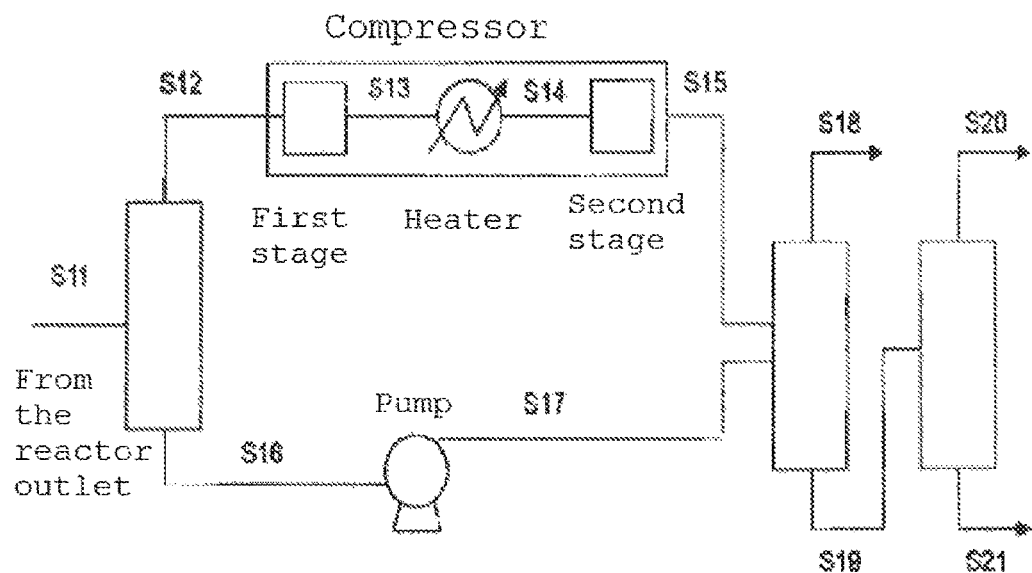
FIG. 1 is a flow chart showing an example of the step of separating a reaction product into multiple components in the method for producing a fluorine-containing halogenated hydrocarbon according to the present invention.

The method for producing a fluorine-containing halogenated hydrocarbon of the present invention (hereinbelow, referred to as "production method of the present invention") is a method for producing a fluorine-containing halogenated hydrocarbon comprising a step of reacting a chlorine-containing compound and hydrogen fluoride in a vapor phase, the method comprising a separation step of separating a reaction product containing hydrogen fluoride, hydrogen chloride, and organic matter containing a fluorine-containing halogenated hydrocarbon into multiple components, the fluorine-containing halogenated hydrocarbon being at least one member selected from the group consisting of 1,1,1,2,2-pentafluoropropane (HFC-245cb), 1,1,1,3,3-pentafluoropropane (HFC-245fa), E,Z-1,3,3,3-tetrafluoropropene (E,Z-HFO-1234ze), 2,3,3,3-tetrafluoropropene (HFO-1234yf), 2-chloro-3,3,3-trifluoropropene (HCFO-1233xf) and 1-chloro-3,3,3-trifluoropropene (HCFO-1233zd), the separation step comprising:

(1) step 1 of separating the reaction product into a gas phase and a liquid phase,
(2) step 2 of increasing the pressure of the liquid phase and supplying the liquid phase into a distillation column A,
(3) step 3 of compressing the gas phase and supplying the gas phase into the distillation column A, and
(4) step 4 of separating a first stream containing the hydrogen chloride from the top of the distillation column A, and separating a second stream containing the organic matter and the hydrogen fluoride from the bottom of the distillation column A, (5) in step 3, the gas phase being compressed in series in two or more stages using a compressor, and heated by a heater to maintain a fraction of compressed gas at each stage of 1.

In the method having the above features according to the present invention, in the separation step of separating a reaction product containing hydrogen fluoride, hydrogen chloride, and organic matter containing a fluorine-containing halogenated hydrocarbon into multiple components, the gas phase is compressed in series in two or more stages using a compressor, and heated by a heater to maintain a fraction of compressed gas at each stage of 1.

According to the production method of the present invention, in an embodiment in which the reaction pressure in a fluorination reaction is reduced to inhibit catalyst deactivation, and gas at the outlet of a fluorination reactor is compressed using a compressor, condensation of hydrogen fluoride contained in the gas at the reactor outlet can be prevented, thus leading to the subsequent distillation step. Accordingly, a fluorine-containing halogenated hydrocarbon, which is a target compound, can be stably obtained without breaking the compressor.

Hereinbelow, the production method of the present invention is explained by each step with reference to FIG. 1

Step 1 Gas-Liquid Separation Step of Reaction Product)

Of the separation steps of separating the reaction product containing hydrogen chloride, hydrogen fluoride, and organic matter containing a fluorine-containing halogenated hydrocarbon into multiple components, step 1 is the step of separating the reaction product into a gas phase and a liquid phase.

When the chlorine-containing compound and the hydrogen fluoride are reacted in a vapor phase in one stage, the reaction product means a reaction product containing a fluorine-containing halogenated hydrocarbon obtained by the one-stage reaction. When the chlorine-containing compound and the hydrogen fluoride are reacted in a vapor phase in multiple stages, the reaction product means a reaction product containing a fluorine-containing halogenated hydrocarbon obtained by the reaction in the final stage.

The production method of the present invention can be applied for the method for producing a fluorine-containing halogenated hydrocarbon comprising the step of reacting a chlorine-containing compound and hydrogen fluoride in a vapor phase. Such a production method is generally performed using a fluorination catalyst, and at least one of chlorine-containing alkanes or chlorine-containing alkenes as a chlorine-containing compound.

Preferable examples of chlorine-containing compounds include at least one member selected from the group consisting of 1,1,1,2,3-pentachloropropane (HCC-240db), 1,1,2,2,3-pentachloropropane (HCC-240aa), 1,1,2,3-tetrachloropropene (HCO-1230xa), 2,3,3,3-tetrachloropropene (HCO-1230xf), 2-chloro-3,3,3-trifluoropropene (HCFO-1233xf), 2,3-dichloro-3,3-difluoropropene (HCFO-1232xf), 1,2,3-trichloro-1,1-difluoropropane (HCFC-242dc), 1-chloro-3,3,3-trifluoropropene (HCFO-1233zd), 2,3-dichloro-1,1,1-trifluoropropane (HCFC-243db), 3,3-dichloro-1,1,1-trifluoropropane (HCFC-243fa), 2-chloro-1,1,1,2-tetrafluoropropane (HCFC-244bb), and 3-chloro-1,1,1,3-tetrafluoropropane (HCFC-244fa). Such chlorine-containing compounds can be used in accordance with the kind of a target compound or the number of reaction stages (one-stage reaction or two or more multiple-stage reaction). Two or more kinds of chlorine-containing compounds can be mixed as necessary for use.

When the target compound is HFO-1234yf, HCFO-1233xf is used as a starting material and is subjected to one-stage vapor-phase fluorination reaction to thereby obtain a reaction product containing HFO-1234yf. When starting materials (chlorine-containing compounds) other than HCFO-1233xf are used, one-stage vapor-phase fluorination reaction may be performed to obtain a reaction product containing HFO-1234yf; however, in order to increase the yield of target product HFO-1234yf, the starting material may be subjected to multiple-stage vapor-phase fluorination reaction to thereby obtain a reaction product containing HFO-1234yf. When the starting material is subjected to multiple-stage (e.g., two-stage) vapor-phase fluorination reaction, the starting material chlorine-containing compound is subjected to vapor-phase fluorination using hydrogen fluoride in the presence of a fluorination catalyst to thereby obtain an intermediate product containing HCFO-1233xf, and then the intermediate product containing HCFO-1233xf is further subjected to vapor-phase fluorination using hydrogen fluoride in the presence of a fluorination catalyst, thus obtaining a reaction product containing HFO-1234yf by two-stage reaction.

When the target compound is HFO-1234yf, preferable examples of the chlorine-containing compound include at least one member selected from the group consisting of 1,1,1,2,3-pentachloropropane (HCC-240db), 1,1,2,2,3-pentachloropropane (HCC-240aa), 1,1,2,3-tetrachloropropene (HCO-1230xa), 2,3,3,3-tetrachloropropene (HCO-1230xf), 2-chloro-3,3,3-trifluoropropene (HCFO-1233xf), 2,3-dichloro-3,3-difluoropropene (HCFO-1232xf), 1,2,3-trichloro-1,1-difluoropropane (HCFC-242dc), 1-chloro-3,3,3-trifluoropropene (HCFO-1233zd), and 2,3-dichloro-1,1,1-trifluoropropane (HCFC-243db), Of these, preferable starting materials are those containing HCFO-1233xf because a reaction product containing target compound HFO-1234yf can be obtained by one-stage vapor-phase fluorination reaction.

Hereinbelow, by representing an example in which HFO-1234yf is the target compound, two-stage reaction including the first reaction step and the second reaction step is explained. When HCFO-1233xf is used as a starting material, the vapor-phase fluorination reaction in the second reaction step is mainly used to obtain a HFO-1234yf-containing reaction product in one stage.

(i) First Reaction Step

In the first reaction step, in the presence of a fluorination catalyst, the aforementioned starting material (chlorine-containing compound: sometimes referred to as a starting material compound) and hydrogen fluoride are reacted under heating in a vapor phase.

In the first reaction step, the reaction of the starting material compound with hydrogen fluoride under the above conditions yields a product containing HCFO-1233xf that is an intermediate for HFO-1234yf.

The first reaction step requires the reaction of the starting material compound with hydrogen fluoride in a vapor phase in the presence of a fluorination catalyst. As long as the starting material compound and hydrogen fluoride come into contact with each other in a gas form within the reaction temperature range described below, the starting material compound may be in a liquid form when supplied. For example, when the starting material compound is liquid at an ordinary temperature and ordinary pressure, it is vaporized using a vaporizer (vaporization region), passed through a preheating region, and then supplied to a mixing region wherein the starting material compound comes into contact with hydrogen fluoride, thereby the reaction can be conducted in a vapor phase. The reaction may also be carried out by supplying the starting material compound in a liquid phase to a reactor, and vaporizing the compound when the compound attains the reaction range with hydrogen fluoride. The reaction may also be carried out by superheating vaporized hydrogen fluoride, supplying the starting material thereto to vaporize the starting material, and supplying the mixture to a reactor.

As a fluorination catalyst used in the first reaction step, a known catalyst that shows activity in fluorination reaction with hydrogen fluoride can be used. Usable examples include metal oxides and fluorinated metal oxides, such as chromium oxide, fluorinated chromium oxide, aluminum fluoride, and fluorinated aluminum oxide. In addition, metal fluorides, such as $MgF_2$, $TaF_5$, and $SbF_5$ can also be used.

Of these catalysts, although there is no limitation, a chromium oxide represented by composition formula: $CrO_m$ wherein $1.5<m<3$ is preferable, a chromium oxide represented by composition formula: $CrO_m$ wherein $2<m<2.75$ is more preferable, and a chromium oxide represented by composition formula: $CrO_m$ wherein $2<m<2.3$ is still more preferable. The chromium oxide catalyst can be of any shape, for example, powder or pellets, as long as it suits the reaction. In particular, pellets are preferable. Such chromium oxide catalysts can be prepared by a method described in JP1993-146680A.

Fluorinated chromium oxide can be prepared by a method described in JP1993-146680A. For example, fluorinated chromium oxide can be prepared by fluorinating the chromium oxide obtained by the above-described method with hydrogen fluoride (HF treatment).

The degree of fluorination is not limited. For example, a fluorinated chromium oxide having a fluorine content of about 10 to 45% by weight may be suitably used.

Further, a chromium-based catalyst disclosed in JP1999-171806A also may be used as a chromium oxide catalyst or fluorinated chromium oxide catalyst. The chromium-based catalyst is in an amorphous state and comprises, as a main component, a chromium compound containing at least one metallic element selected from the group consisting of indium, gallium, cobalt, nickel, zinc, and aluminum. The chromium in the chromium compound has an average valence number of not less than +3.5 and not more than +5.0.

The above-described fluorination catalyst may be used as supported on a carrier such as alumina and activated carbon. There is no limitation to the methods for vaporizing the starting material compound in the reaction range. The starting material compound may be vaporized into a vapor phase by, for example, filling a preheating region with a material that exhibits excellent thermal conductivity, exerts no catalytic activity in the reaction of the present invention, and is stable to hydrogen fluoride, such as metal pieces of corrosion-resistant materials including nickel beads, alumina beads, Hastelloy, Inconel, Monel, Incolloy, and the like, so as to heat the preheating region to not less than the vaporization temperature of the starting material compound; and supplying the starting material compound in a liquid phase thereinto.

Hydrogen fluoride may generally be supplied to a reactor in the form of a vapor phase together with the starting material compound. The amount of hydrogen fluoride to be supplied is generally about 1 to 100 moles, preferably about 5 to 50 moles, and more preferably about 10 to 30 moles, per mole of the starting material compound. By setting the amount within such a range, the conversion of the starting material compound and the selectivity of components, such as HCFO-1233xf, that can be intermediates for 2,3,3,3-tetrafluoropropene (HFO-1234yf), can be maintained within an excellent range.

The starting material may be supplied to the reactor as is or may be diluted with an inert gas such as nitrogen, helium, or argon, and then supplied to the reactor.

The form of the reactor used in the first reaction step is not limited. Examples of usable reactors include an adiabatic reactor packed with a catalyst. Also usable is a multitubular reactor or the like in which a heating medium is used to cool the reactor and to homogenize the temperature distribution within the reactor.

The reactor is preferably made of an alloy containing 30% or more by weight of nickel. More specifically, a reactor formed of a material that is resistant to the corrosive action of hydrogen fluoride, such as Hastelloy, Inconel, Monel, and Incolloy, is preferably used.

In the first reaction step, the reaction temperature, i.e., the temperature in the reactor, is about 200 to 500° C., preferably about 250 to 400° C., and more preferably about 300 to 350° C. If the reaction temperature is higher than this range, the selectivity of components, such as HCFO-1233xf, that can be intermediates for HFO-1234yf undesirably decreases. If the reaction temperature is lower than this range, the conversion of the starting material compound undesirably decreases.

The pressure during the reaction is not limited, as long as the starting material compound and hydrogen fluoride can be present in a vapor phase, and the reaction may be conducted under ordinary pressure or increased pressure. More specifically, the first reaction step may be conducted under atmospheric pressure (0.1 MPa). This step also may be conducted under increased pressure and temperature condition at which the starting material does not turn into a liquid phase.

The reaction time is not limited. The residence time, which is represented by W/Fo, may be generally adjusted to a range of about 1 to 10 (g·sec/cc). W/Fo is the ratio of the catalyst weight W (g) in a vapor phase to the total flow rate Fo (flow rate at 0° C., 0.1 MPa: cc/sec) of the starting material gases (starting material compound, hydrogen fluoride, and inert gas) supplied to the reaction system.

Under the above reaction conditions, a reaction product containing HCFO-1233xf can be obtained at the reactor outlet.

(ii) Second Reaction Step

In the second reaction step, the product obtained in the first reaction step is used as a starting material and reacted with hydrogen fluoride in a vapor phase in the presence of a fluorination catalyst under heating.

The product obtained in the first reaction step contains HCFO-1233xf as a main component and may also contain a chloropropane compound, such as 1,2,3-trichloro-1,1-difluoropropane (HCFC-242dc) and 2,3-dichloro-3,3-difluoropropane (HCFO-1232xf), or a chloropropene compound. When the product containing a chloropropane compound, chloropropene compound, or the like is used as is as a starting material and reacted with hydrogen fluoride in the presence of a fluorination catalyst in the second reaction step, not only HCFO-1233xf but also the components contained in the product, such as HCFC-242dc and HCFO-1232xf, can be converted to HFO-1234yf. As a result, the desired HFO-1234yf can be obtained with high selectivity.

As a fluorination catalyst used in the second reaction step, a known catalyst having activity to a fluorination reaction with hydrogen fluoride may be used. For example, metal oxides or metal oxyfluorides, such as chromium oxides, chromium oxyfluorides, aluminium fluorides, and aluminum oxyfluorides may be used. In addition to these catalysts, metal fluorides, such as $MgF_2$, $TaF_5$, and $SbF_5$ also may be used.

Of these catalysts, although there is no limitation, a chromium oxide represented by composition formula: CrOm wherein 1.5<m<3 is preferable, a chromium oxide represented by composition formula: CrOm wherein 2<t<2.75 is more preferable, and a chromium oxide represented by composition formula: CrOm wherein 2<m<2.3 is still more preferable. Any chromium oxide catalysts in the form of powder, pellets, etc., can be used, as long as they are suitable for the reaction. In particular, pellet-form catalysts are preferred. The above chromium oxide catalysts can be produced, for example, by the process disclosed in JP1993-146680A.

In addition, the fluorinated chromium oxides can be prepared by the process disclosed in JP1993-146680A. For example, they can be prepared by fluorinating the chromium oxide obtained by the above-described process with hydrogen fluoride (HF treatment).

The degree of fluorination is not limited. For example, a fluorinated chromium oxide having a fluorine content of about 10 to 45% by weight may be suitably used.

Further, a chromium-based catalyst disclosed in JP1999-171806A also may be used as a chromium oxide catalyst or fluorinated chromium oxide catalyst. The chromium-based catalyst is in an amorphous state and comprises, as a main component, a chromium compound containing at least one metallic element selected from the group consisting of indium, gallium, cobalt, nickel, zinc, and aluminum. The chromium in the chromium compound has an average valence number of not less than +3.5 and not more than +5.

The above-described fluorination catalyst may be used as supported on a carrier such as alumina and activated carbon.

Hydrogen fluoride used as a starting material may be generally supplied to a reactor in the form of vapor phase together with the reaction product obtained in the first reaction step. The amount of hydrogen fluoride supplied in the second reaction step is generally about 1 to 50 moles, preferably about 5 to 30 moles, and more preferably about 7 to 20 moles, per mole of the reaction product obtained in the first reaction step. The amount of hydrogen fluoride supplied in the second reaction step is preferably within the above-described range and smaller than the amount of hydrogen fluoride actually supplied in the first reaction step.

When the amount of hydrogen fluoride contained in the reaction product obtained in the first reaction step is within the aforementioned range, a fluorination reaction in the second reaction step can be conducted by using only the reaction product obtained in the first reaction step, without adding further hydrogen fluoride. When the amount of hydrogen fluoride contained in the reaction product obtained in the first reaction step is larger than the aforementioned range, the reaction product may be used as a starting material in the second reaction step after reducing the amount of hydrogen fluoride contained therein by a method such as distillation.

The selectivity of HFO-1234yf can be maintained in a desirable range by using anhydrous hydrogen fluoride within the above-described range in the presence of a fluorination catalyst.

To maintain catalyst activity for a long period of time, oxygen may be supplied to the reactor as entrained with the aforementioned starting material, especially in the second reaction step. In this case, the amount of oxygen to be supplied may be about 0.01 to 0.3 mole per mole of the reaction product obtained in the first reaction step.

The form of the reactor used in the second reaction step is not limited, Examples of usable reactors include an adiabatic reactor packed with a catalyst and a multitubular reactor in which a heating medium is used to cool the reactor. As in the first reaction step, a reactor formed of a material that is resistant to the corrosive action of hydrogen fluoride, such as Hastelloy, Inconel, and Monel, is preferably used.

In the second reaction step, the reaction temperature, i.e., the temperature in the reactor, is about 200 to 500° C., preferably about 300 to 450° C., and more preferably about 350 to 400° C. If the reaction temperature is higher than this range, the selectivity of HFO-1234yf undesirably decreases. If the reaction temperature is lower than this range, the conversion of the starting material compound undesirably decreases. In particular, the reaction temperature in the second reaction step is preferably within the above-described range and lower than that in the first reaction step.

The pressure during the reaction is not limited, and the reaction may be conducted under ordinary pressure or increased pressure. More specifically, the reaction in the present invention may be conducted under atmospheric pressure (0.1 MPa), and may be also conducted under an increased pressure up to about 0.5 MPa.

The reaction time is not particularly limited. However, the contact time, which is represented by W/Fo, may be generally adjusted to a range of about 5 to 20 g® sec/cc. W/Fo is the ratio of the amount of packed catalyst W(g) to the total flow rate of the starting material gases supplied to the reactor in the second reaction step (total amount of product obtained in the first reaction step and HF) Fo (flow rate at 0° C., 1 atm: cc/sec).

(iii) Reaction Product

According to the aforementioned process comprising the two-stage reaction step, the reaction product that contains the desired HFO-1234yf can be obtained with high selectivity at the reactor outlet in the second reaction step.

The reaction product contains unreacted hydrogen fluoride and hydrogen chloride, and organic matter containing HFO-1234yf. Although the kind of organic matter containing HFO-1234yf depends on the kind of starting material, examples of organic matter other than HFO-1234yf include HCFO-1233xf, 1,1,1,2,2-pentafluoropropane (HFC-245cb), HCFO-1233zd, 1,3,3,3-tetrafluoropropene (HFO-1234ze), and the like.

In step 1, the reaction product (S11 in FIG. 1) containing a fluorine-containing halogenated hydrocarbon (HFO-1234yf in the above examples) is separated into a gas phase (S12) and a liquid phase (S16). A known gas liquid separator can be used for separating the reaction product into a gas phase and a liquid phase. From the viewpoint of efficient separation, a cooler (condenser) is preferably used. By the gas liquid separation, most of the hydrogen fluoride is separated into a liquid phase, a small amount of the hydrogen fluoride is separated into a gas phase, and substantially all of the hydrogen chloride is separated into a gas phase.

Step 2 (Step of Increasing the Pressure of the Liquid Phase and Supplying the Liquid Phase to the Distillation Column A)

In step 2, the pressure of the liquid phase separated in step 1 is increased, and the liquid phase is supplied to the distillation column A.

A pump can be used for increasing the pressure of the liquid phase. It is necessary to set pressure increase conditions so that the pump discharge pressure is higher than the operating pressure of the distillation column A, and the pressure is preferably 5 to 10% higher than the operating pressure of the distillation column.

Step 3 (Step of Compressing the Gas Phase and Supplying the Gas Phase to the Distillation Column A)

Step 3 is the step of supplying the gas phase separated in step 1 to the distillation column A. Specifically, the gas phase is compressed in series in two or more stages using a compressor, and the gas phase is heated by a heater to thereby maintain the fraction of gas after compression in each stage at 1. The gas fraction is represented by the amount of gas phase/(amount of liquid phase+amount of gas phase) based on a mole.

While the gas phase is compressed in series in two or more stages and is supplied to the distillation column A, as long as the fraction of gas after compression in each stage can be maintained at 1, the number and location of heaters are not limited. The temperature of the heater is not limited as long as the fraction of gas after compression in each stage can be maintained at 1, and it is preferably 0 to 150° C. In this temperature range, when n compressors are disposed in series for performing n stage compression, it is preferable to dispose n−1 heaters between stages. In the production method of the present invention, it is preferable to maintain the fraction of gas obtained from the first stage compression at 1 until the gas reaches the distillation column A through the multiple stages.

In FIG. 1, as a compressor for compressing the gas phase, two compressors, i.e., a first stage compressor and a second stage compressor are provided, and a heater is disposed between the first and second stage compressors. By performing compression at each stage under heating with a heater, the fraction of compressed gas at each stage is maintained at 1. The temperature of the heater is not limited; however, when one heater is disposed between the first and second stage compressors as described above, the temperature of the heater is preferably 100° C. or less, and more preferably 30 to 80° C.

In the present invention, when the gas phase is compressed in series in two or more stages, the gas phase in each stage is compressed by a factor of 2 or more. For example, when compression is performed in two stages, the gas phase in each stage is preferably compressed by a factor of 2 to 5.

Step 4 (Step of Performing Distillation in Distillation Column A)

In step 4, the first stream (S18) containing hydrogen chloride is separated from the top of the distillation column A, and the second stream (S19) containing the organic matter and hydrogen fluoride is separated from the bottom of the distillation column A.

Distillation in the distillation column A is performed according to a known method. The operating pressure of the distillation column can be selected between 0.1 to 2 MPa. Since the condensation temperature becomes higher as the pressure increases, cooling cost can be reduced; however, considering the cost increase due to increased device thickness or leakage risk resulting from increased pressure, a suitable pressure is selected.

The second stream separated from the bottom of the distillation column A usually contains hydrogen fluoride and organic matter containing a side product, unreacted starting material, or target fluorine-containing halogenated hydrocarbon.

Step 5 (Step of Performing Distillation in Distillation Column B)

The production method of the present invention may further comprise the step of supplying the second stream to the distillation column B, and separating the second stream by distillation into the third stream (e.g., S20) containing the fluorine-containing halogenated hydrocarbon and the fourth stream (e.g., S21) containing hydrogen fluoride and organic matter other than the fluorine-containing halogenated hydrocarbon. In this step, the second stream containing target organic matter is subjected to fractional distillation to separate the target compound. Distillation conditions can be suitably determined in accordance with the kind of the target compound, difference in boiling point, etc. As the distillation column B, those capable of performing multistage distillation can be used as necessary. In this case, distillation conditions can be determined in a manner such that the target compound can be more finely separated.

Distillation in the distillation column B can be performed according to a known method. The operating pressure of the distillation column can be selected between 0.1 to 2 MPa, as in the distillation column A. Operating the distillation column A at a pressure higher than that of the distillation column 8 will eliminate the need for compression between the distillation columns, and thus, is convenient.

The third stream containing the fluorine-containing halogenated hydrocarbon includes a composition mainly containing the target fluorine-containing halogenated hydrocarbon. The fluorine-containing halogenated hydrocarbon can be further subjected to a crude purification step and a fine purification step to yield a final product. Specific methods for the crude purification step and the fine purification step are not limited. For example, water washing, dehydration (drying), additional distillation, liquid-liquid separation, or other means can be applied to these steps.

The fourth stream containing hydrogen fluoride and organic matter other than the fluorine-containing halogenated hydrocarbon generally contains hydrogen fluoride and organic matter other than the target compound of fluorine-containing halogenated hydrocarbon. After the components contained in the fourth stream have suitably undergone a crude purification step, they can be recycled for vapor-phase fluorination reaction of the chlorine-containing compound and hydrogen fluoride in the present invention.

In the production method of the present invention, steps 1 to 5 can be performed in this order; however, steps 2 and 3 can be performed in random order or at the same time.

EXAMPLES

The present invention is detailed below with reference to Examples and Comparative Examples; however, the present invention is not limited thereto. Examples and Comparative Examples are based on simulation.

Example 1

The flow rate (mol/h) of each stream (S11 to S21) obtained in the separation of gas at the outlet of a fluorination reactor into multiple components as shown in FIG. 1 was examined. Table 1 shows the flow rate. Example 1 is a method for producing HFO-1234yf as a target compound.

TABLE 1

| Mole flow Kmol/hr | S11 | S12 | S13 | S14 | S15 | S16 | S17 | S18 | S19 | S20 | S21 |
|---|---|---|---|---|---|---|---|---|---|---|---|
| HF | 1.85 | 0.059 | 0.059 | 0.059 | 0.059 | 1.79 | 1.79 | 0.000 | 1.85 | 0.025 | 1.82 |
| HCL | 0.028 | 0.028 | 0.028 | 0.028 | 0.028 | 0.000 | 0.000 | 0.028 | 0.000 | 0.000 | 0.000 |
| 1233XF | 0.066 | 0.010 | 0.010 | 0.010 | 0.010 | 0.056 | 0.056 | 0.000 | 0.066 | 0.000 | 0.066 |
| 1234YF | 0.028 | 0.018 | 0.018 | 0.018 | 0.018 | 0.010 | 0.010 | 0.000 | 0.028 | 0.028 | 0.000 |
| 245CB | 0.012 | 0.008 | 0.008 | 0.008 | 0.008 | 0.004 | 0.004 | 0.000 | 0.012 | 0.011 | 0.000 |
| 1233ZD | 0.002 | 0.000 | 0.000 | 0.000 | 0.000 | 0.002 | 0.002 | 0.000 | 0.002 | 0.000 | 0.002 |
| E1234ZE | 0.004 | 0.003 | 0.003 | 0.003 | 0.003 | 0.001 | 0.001 | 0.000 | 0.004 | 0.000 | 0.003 |
| Other | 0.013 | 0.009 | 0.009 | 0.009 | 0.009 | 0.004 | 0.004 | 0.009 | 0.004 | 0.000 | 0.003 |
| Temperature (° C.) | 146 | −20 | 10.8 | 35 | 72.0 | −1.5 | −1.0 | −37.8 | 61.9 | 42.6 | 81.6 |
| Pressure (MPaG) | 0.02 | 0.005 | 0.23 | 0.23 | 0.95 | 0.005 | 0.95 | 0.9 | 0.95 | 0.86 | 0.91 |
| Vapor fraction | 1 | 1 | 1 | 1 | 1 | 0 | 0 | 1 | 0 | 1 | 0 |

Vapor fraction: Amount of gas phase/(amount of liquid phase+amount of gas phase) based on mole

Comparative Example 1

Figure 2:
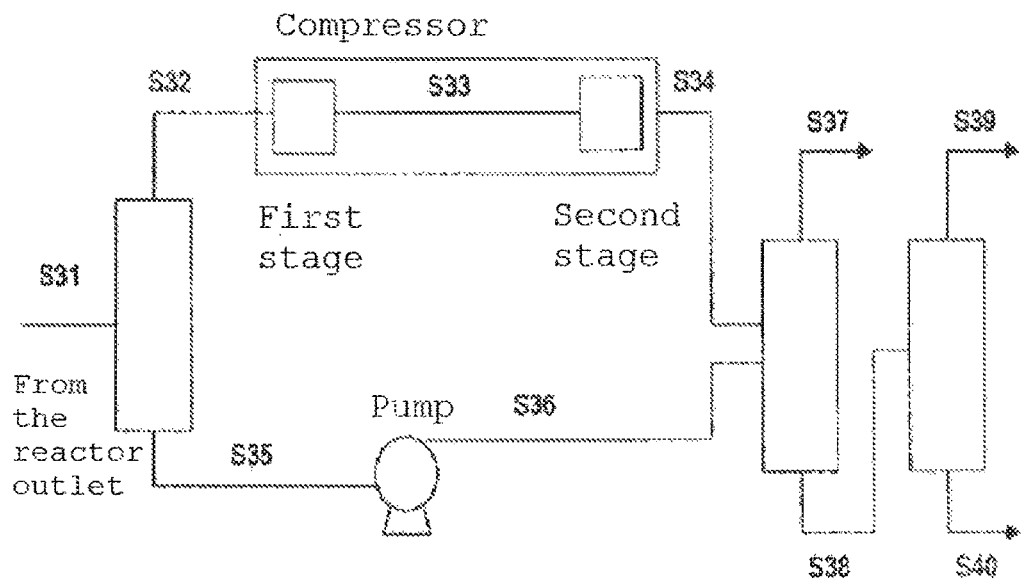
FIG. 2 is a flow chart showing an example of the step of separating a reaction product into multiple components in a conventional method for producing a fluorine-containing halogenated hydrocarbon.

The flow rate (mol/h) of each stream (S31 to S40) obtained in the separation of gas at the outlet of a fluorination reactor into multiple components as shown in FIG. 2 was examined. The same conditions as in FIG. 1 were used except that the heater was not disposed between the first stage and the second stage compression using a compressor. Table 2 shows the flow rate, Comparative Example 1 is a method for producing HFO-1234yf as a target compound.

TABLE 1

| Mole flow Kmol/hr | S31 | S32 | S33 | S34 | S35 | S36 | S37 | S38 | S39 | S40 |
|---|---|---|---|---|---|---|---|---|---|---|
| HF | 1.85 | 0.059 | 0.059 | 0.059 | 1.79 | 1.79 | 0.000 | 1.85 | 0.025 | 1.82 |
| HCL | 0.028 | 0.028 | 0.028 | 0.028 | 0.000 | 0.000 | 0.028 | 0.000 | 0.000 | 0.000 |
| 1233XF | 0.066 | 0.010 | 0.010 | 0.010 | 0.056 | 0.056 | 0.000 | 0.066 | 0.000 | 0.066 |
| 1234YF | 0.028 | 0.018 | 0.018 | 0.018 | 0.010 | 0.010 | 0.000 | 0.028 | 0.028 | 0.000 |
| 245CB | 0.012 | 0.008 | 0.008 | 0.008 | 0.004 | 0.004 | 0.000 | 0.012 | 0.011 | 0.000 |
| 1233ZD | 0.002 | 0.000 | 0.000 | 0.000 | 0.002 | 0.002 | 0.000 | 0.002 | 0.000 | 0.002 |
| E1234ZE | 0.004 | 0.003 | 0.003 | 0.003 | 0.001 | 0.001 | 0.000 | 0.004 | 0.004 | 0.000 |
| Other | 0.013 | 0.009 | 0.009 | 0.009 | 0.004 | 0.004 | 0.009 | 0.004 | 0.000 | 0.003 |
| Temperature (° C.) | 146 | −20 | 10.8 | 47.2 | −1.5 | −1.0 | −37.8 | 61.9 | 42.6 | 81.6 |
| Pressure (MPaG) | 0.02 | 0.005 | 0.23 | 0.95 | 0.005 | 0.95 | 0.9 | 0.95 | 0.86 | 0.91 |
| Vapor fraction | 1 | 1 | 1 | 0.94 | 0 | 0 | 1 | 0 | 1 | 0 |

As is clear from the results of Tables 1 and 2, the gas fraction during compression of the gas phase was maintained at 1 in Example 1, thus making it possible to stably lead to the subsequent distillation step. In Comparative Example 1, however, the gas phase liquefied at the first stage of compression of the gas phase, and the compressor did not function, making it impossible to stably lead to the subsequent distillation step.

S11, S31 Inlet of gas liquid separation device
S12, S32 Inlet of compressor
S13, S33 Outlet of compression first stage
S14 Outlet of heater
S15, S34 Outlet of compressor
S16, S35 Inlet of pump
S17, S36 Outlet of pump
S18, S37 Top of distillation column A
S19, S38 Bottom of distillation column A
S20, S39 Top of distillation column B
S21, S40 Bottom of distillation column B

The invention claimed is:

1. A method for producing a fluorine-containing halogenated hydrocarbon comprising the step of reacting a chlorine-containing compound and hydrogen fluoride in a vapor phase,
the method comprising a separation step of separating a reaction product containing hydrogen fluoride, hydrogen chloride, and organic matter containing the fluorine-containing halogenated hydrocarbon into multiple components,
the fluorine-containing halogenated hydrocarbon being at least one member selected from the group consisting of 1,1,1,2,2-pentafluoropropane (HFC-245cb), 1,1,1,3,3-pentafluoropropane (HFC-245fa), E,Z-1,3,3,3-tetrafluoropropene (E,Z-HFO-1234ze), 2,3,3,3-tetrafluoropropene (HFO-1234yf), 2-chloro-3,3,3-trifluoropropene (HCFO-1233xf), and 1-chloro-3,3,3-trifluoropropene (HCFO-1233zd),
the separation step comprising:
(1) step 1 of separating the reaction product into a gas phase and a liquid phase,
(2) step 2 of increasing the pressure of the liquid phase and supplying the liquid phase into a distillation column A,
(3) step 3 of compressing the gas phase and supplying the gas phase into the distillation column A, and
(4) step 4 of separating a first stream containing the hydrogen chloride from the top of the distillation column A, and separating a second stream containing the organic matter and the hydrogen fluoride from the bottom of the distillation column A,
(5) in step 3, the gas phase being compressed in series in two or more stages using a compressor, and heated by a heater to maintain a fraction of compressed gas in each stage at 1.

2. The method according to claim 1, wherein the chlorine-containing compound is at least one member of chlorine-containing alkanes or chlorine-containing alkenes.

3. The method according to claim 1, wherein the chlorine-containing compound is at least one member selected from the group consisting of 1,1,1,2,3-pentachloropropane (HCC-240db), 1,1,2,2,3-pentachloropropane (HCC-240aa), 1,1,2,3-tetrachloropropene (HCO-1230xa), 2,3,3,3-tetrachloropropene (HCO-1230xf), 2-chloro-3,3,3-trifluoropropene (HCFO-1233xf), 2,3-dichloro-3,3-difluoropropene (HCFO-1232xf), 1,2,3-trichloro-1,1-difluoropropane (HCFC-242dc), 1-chloro-3,3,3-trifluoropropene (HCFO-1233zd), 2,3-dichloro-1,1,1-trifluoropropane (HCFC-243db), 3,3-dichloro-1,1,1-trifluoropropane (HCFC-243fa), 2-chloro-1,1,1,2-tetrafluoropropane (HCFC-244bb), and 3-chloro-1,1,1,3-tetrafluoropropane (HCFC-244fa).

4. The method according to claim 1, wherein the fluorine-containing halogenated hydrocarbon comprises HFO-1234yf, and the chlorine-containing compound is at least one member selected from the group consisting of 1,1,1,2,3-pentachloropropane (HCC-240db), 1,1,2,2,3-pentachloropropane (HCC-240aa), 1,1,2,3-tetrachloropropene (HCO-1230xa), 2,3,3,3-tetrachloropropene (HCO-1230xf), 2-chloro-3,3,3-trifluoropropene (HCFO-1233xf), 2,3-dichloro-3,3-difluoropropene (HCFO-1232xf), 1,2,3-trichloro-1,1-difluoropropane (HCFC-242dc), 1-chloro-3,3,3-trifluoropropene (HCFO-1233zd), and 2,3-dichloro-1,1,1-trifluoropropane (HCFC-243db).

5. The method according to claim 1, wherein the fluorine-containing halogenated hydrocarbon comprises HFO-1234yf, and the chlorine-containing compound comprises HCFO-1233xf.

6. The method according to claim 1, wherein the molar ratio of the hydrogen fluoride to the chlorine-containing compound at the beginning of the reaction of the chlorine-containing compound and the hydrogen fluoride in a vapor phase is 10 or more.

7. The method according to claim 1, wherein when the gas phase is compressed in series in two or more stages in step 3, the compression rate at each stage is 2 times or more.

8. The method according to claim 1, further comprising the step of supplying the second stream into a distillation column B, and separating the second stream into a third stream containing the fluorine-containing halogenated hydrocarbon and a fourth stream containing the hydrogen fluoride and organic matter other than the fluorine-containing halogenated hydrocarbon by distillation.

* * * * *